(12) United States Patent
Macchi (10) Patent No.: US 9,867,678 B2
(45) Date of Patent: *Jan. 16, 2018

(54) ORTHODONTIC BRACKET HAVING AN ARCHWIRE CHANNEL AND ARCHWIRE RETAINING MECHANISM

(71) Applicant: RMO, Inc., Denver, CO (US)

(72) Inventor: Aldo Macchi, Varese (IT)

(73) Assignee: RMO, Inc., Denver, CO (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/860,028

(22) Filed: Sep. 21, 2015

(65) Prior Publication Data

US 2016/0008099 A1     Jan. 14, 2016

Related U.S. Application Data

(63) Continuation of application No. 13/939,937, filed on Jul. 11, 2013, now Pat. No. 9,144,473, which is a
(Continued)

(51) Int. Cl.
*A61C 3/00* (2006.01)
*A61C 7/14* (2006.01)
(Continued)

(52) U.S. Cl.
CPC ............ *A61C 7/143* (2013.01); *A61C 7/14* (2013.01); *A61C 7/145* (2013.01); *A61C 7/16* (2013.01); *A61C 7/20* (2013.01); *A61C 7/28* (2013.01)

(58) Field of Classification Search
CPC .... A61C 7/14; A61C 7/00; A61C 7/02; A61C 7/12; A61C 7/28; A61C 7/143; A61C 7/148
(Continued)

(56) References Cited

U.S. PATENT DOCUMENTS 626,476 A    6/1899   Angle
1,890,487 A  12/1932  Angle
(Continued)

FOREIGN PATENT DOCUMENTS

DE   8903611    8/1990
DE   69228472   10/1999
(Continued)

OTHER PUBLICATIONS

U.S. Appl. No. 10/821,699, filed Apr. 9, 2004, Ricketts.
(Continued)

*Primary Examiner* — Matthew Nelson
(74) *Attorney, Agent, or Firm* — Sheridan Ross P.C.

(57) ABSTRACT

An orthodontic bracket is disclosed having three archwire retention channels in the mesial-distal directions, a central channel and two side channels. The two side channels each include a pair of spaced apart inverted archwire retaining regions having a recess that opens generally towards the bracket base. Each such recess is for grasping or holding an archwire therein. Each of the side channels has an archwire retaining ridge extending gingivally-occlusally along the adjacent side of the bracket base between the two retaining regions of the channel. For each channel, its retaining ridge exerts a force on a portion of an archwire facing away from the archwire portion residing in the recesses of the retaining regions of the channel. The force on the archwire is directed toward the interiors of the recesses of the retaining regions for assisting in seating the archwire in the recesses.

20 Claims, 7 Drawing Sheets

Related U.S. Application Data continuation of application No. 12/724,159, filed on Mar. 15, 2010, now Pat. No. 8,485,816.

(60) Provisional application No. 61/160,653, filed on Mar. 16, 2009.

(51) Int. Cl.
  *A61C 7/28* (2006.01)
  *A61C 7/16* (2006.01)
  *A61C 7/20* (2006.01)

(58) Field of Classification Search
  USPC .................................................. 433/8–24
  See application file for complete search history.

(56) References Cited

U.S. PATENT DOCUMENTS

| | | |
|---|---|---|
| 2,011,575 A | 8/1935 | Ford |
| 2,104,192 A | 1/1938 | Fard |
| 2,196,515 A | 4/1940 | Atkinson |
| 3,028,671 A | 4/1962 | Berger |
| 3,055,110 A | 9/1962 | Kesling |
| 3,158,934 A | 12/1964 | Waldman |
| 3,193,930 A * | 7/1965 | Bien ................. A61C 7/12 433/15 |
| 3,391,461 A | 7/1968 | Johnson |
| 3,435,527 A | 4/1969 | Kesling |
| 3,494,034 A | 2/1970 | Kesling |
| 3,504,438 A | 4/1970 | Wittman et al. |
| 3,526,961 A | 9/1970 | Kesling |
| 3,765,091 A | 10/1973 | Northcutt |
| 3,798,773 A | 3/1974 | Northcutt |
| 3,838,514 A | 10/1974 | Polak |
| 3,854,207 A | 12/1974 | Wildman |
| 3,874,080 A | 4/1975 | Wallshein |
| 3,916,526 A | 11/1975 | Schudy |
| 3,964,156 A | 6/1976 | Williams et al. |
| 3,975,824 A | 8/1976 | Lee |
| 3,985,282 A | 10/1976 | Miller et al. |
| 3,987,547 A | 10/1976 | Moss |
| 4,015,334 A | 4/1977 | Moss |
| 4,028,809 A | 6/1977 | Wallshein |
| 4,083,113 A | 4/1978 | Miller et al. |
| 4,103,423 A | 8/1978 | Kessel |
| 4,134,208 A | 1/1979 | Pearlman |
| 4,171,568 A | 10/1979 | Forster |
| 4,172,999 A | 10/1979 | Leidich |
| 4,183,141 A | 1/1980 | Dellinger et al. |
| 4,192,070 A | 3/1980 | Lemchen et al. |
| 4,193,195 A | 3/1980 | Merkel et al. |
| 4,197,642 A | 4/1980 | Wallshein |
| 4,212,638 A | 7/1980 | Korn |
| 4,219,617 A | 8/1980 | Wallshein |
| D256,950 S | 9/1980 | Sable |
| 4,242,085 A | 12/1980 | Wallshein |
| 4,248,587 A | 2/1981 | Kurz |
| 4,260,375 A | 4/1981 | Wallshein |
| 4,284,405 A | 8/1981 | Dellinger |
| 4,299,569 A | 11/1981 | Frantz |
| 4,302,532 A | 11/1981 | Wallshein |
| 4,322,206 A | 3/1982 | Reynolds |
| 4,350,487 A | 9/1982 | Kesling et al. |
| 4,354,834 A | 10/1982 | Wilson |
| 4,386,908 A | 6/1983 | Kurz |
| 4,415,330 A | 11/1983 | Daisley et al. |
| 4,419,078 A | 12/1983 | Pletcher |
| 4,430,061 A | 2/1984 | Webb et al. |
| 4,455,137 A | 6/1984 | Diamond |
| 4,462,800 A | 7/1984 | Jones |
| 4,478,577 A | 10/1984 | Warren, Jr. |
| 4,498,867 A | 2/1985 | Kesling |
| 4,511,331 A | 4/1985 | Scebold et al. |
| 4,527,975 A | 7/1985 | Ghafari et al. |
| 4,529,382 A | 7/1985 | Creekmore |
| 4,531,911 A | 7/1985 | Creekmore |
| 4,531,991 A | 7/1985 | Ziemek et al. |
| 4,545,760 A | 10/1985 | Forster |
| 4,551,095 A | 11/1985 | Mason |
| 4,575,337 A * | 3/1986 | Fujita ................. A61C 7/143 433/15 |
| 4,626,209 A | 12/1986 | Tsai et al. |
| 4,639,218 A | 1/1987 | Jones et al. |
| 4,659,309 A | 4/1987 | Merkel |
| 4,661,059 A | 4/1987 | Kanno |
| D290,040 S | 5/1987 | Kelly |
| 4,669,979 A | 6/1987 | Snead |
| 4,669,981 A | 6/1987 | Kurz |
| 4,674,978 A * | 6/1987 | Acevedo ............. A61C 7/143 433/8 |
| 4,675,978 A | 6/1987 | Swartz |
| D291,919 S | 9/1987 | Reynolds |
| 4,700,697 A | 10/1987 | Mundell et al. |
| 4,712,999 A | 12/1987 | Rosenberg |
| 4,752,221 A | 6/1988 | Hanson et al. |
| 4,773,853 A | 9/1988 | Kussick |
| 4,781,334 A | 11/1988 | Derichs |
| 4,781,582 A | 11/1988 | Kesling |
| 4,793,804 A | 12/1988 | Schudy |
| 4,795,342 A | 1/1989 | Jones |
| 4,799,882 A | 1/1989 | Kesling |
| 4,819,316 A | 4/1989 | Rossini et al. |
| 4,820,151 A | 4/1989 | Pospisil |
| 4,838,786 A | 6/1989 | Reher et al. |
| 4,854,866 A | 8/1989 | Wilson |
| 4,859,179 A | 8/1989 | Kesling |
| 4,900,251 A | 2/1990 | Andreasen |
| 4,917,602 A | 4/1990 | Broussard |
| 4,927,360 A | 5/1990 | Pospisil |
| 4,927,362 A | 5/1990 | Snead |
| 4,954,080 A | 9/1990 | Kelly et al. |
| 4,963,092 A | 10/1990 | Snead |
| 4,975,052 A | 12/1990 | Spencer et al. |
| 4,997,182 A | 3/1991 | Kussick |
| 5,022,854 A | 6/1991 | Broughton et al. |
| 5,030,089 A | 7/1991 | Kawaguchi |
| 5,035,614 A | 7/1991 | Greenfield |
| 5,044,945 A | 9/1991 | Peterson |
| 5,057,012 A | 10/1991 | Kesling |
| 5,059,119 A | 10/1991 | Snead |
| 5,062,794 A | 11/1991 | Miura |
| 5,066,225 A | 11/1991 | Forbes Jones et al. |
| D322,482 S | 12/1991 | Ianieri et al. |
| 5,095,602 A | 3/1992 | Reher et al. |
| 5,120,218 A | 6/1992 | Hanson |
| 5,125,831 A | 6/1992 | Pospisil |
| 5,125,832 A | 6/1992 | Kesling |
| 5,133,740 A | 7/1992 | Suyama |
| 5,151,028 A | 9/1992 | Snead |
| 5,154,607 A | 10/1992 | Hanson |
| 5,158,452 A | 10/1992 | Franseen et al. |
| 5,160,261 A | 11/1992 | Peterson |
| 5,161,969 A | 11/1992 | Pospisil et al. |
| D331,975 S | 12/1992 | Pospisil |
| 5,183,388 A | 2/1993 | Kumar |
| 5,203,804 A | 4/1993 | Nikutowski et al. |
| 5,224,858 A | 7/1993 | Hanson |
| 5,226,814 A | 7/1993 | Allen |
| 5,230,620 A | 7/1993 | Watanabe |
| 5,238,402 A | 8/1993 | Rohlcke et al. |
| 5,242,299 A | 9/1993 | Yoshida |
| D340,523 S | 10/1993 | Barngrover |
| 5,252,066 A | 10/1993 | Fairhurst |
| 5,254,002 A | 10/1993 | Reher et al. |
| 5,267,855 A | 12/1993 | Tuneberg |
| 5,269,680 A | 12/1993 | Kawaguchi |
| 5,277,581 A | 1/1994 | Peterson |
| 5,288,229 A | 2/1994 | Huff et al. |
| 5,292,248 A | 3/1994 | Schultz |
| 5,299,934 A | 4/1994 | Suyama |
| 5,302,117 A | 4/1994 | Kraut et al. |
| 5,302,121 A | 4/1994 | Gagin |
| 5,320,525 A | 6/1994 | Forster |
| 5,320,526 A | 6/1994 | Tuneberg |

(56) References Cited

U.S. PATENT DOCUMENTS

| | | | |
|---|---|---|---|
| 5,322,435 A | 6/1994 | Pletcher | |
| 5,322,613 A | 6/1994 | Ohira | |
| 5,356,288 A | 10/1994 | Cohen | |
| 5,358,402 A | 10/1994 | Reed et al. | |
| 5,362,232 A | 11/1994 | Franseen et al. | |
| 5,362,233 A | 11/1994 | Thompson | |
| 5,380,196 A | 1/1995 | Kelly et al. | |
| 5,383,784 A | 1/1995 | Sernetz | |
| 5,395,238 A | 3/1995 | Andreiko et al. | |
| D358,649 S | 5/1995 | Moschik | |
| D358,650 S | 5/1995 | Moschik | |
| D359,776 S | 6/1995 | Hilgers | |
| 5,439,379 A | 8/1995 | Hansen | |
| 5,441,408 A | 8/1995 | Moschik | |
| 5,441,409 A | 8/1995 | Tuneberg | |
| 5,443,384 A | 8/1995 | Franseen et al. | |
| 5,454,716 A | 10/1995 | Banerjee et al. | |
| 5,464,349 A | 11/1995 | Andreiko et al. | |
| 5,470,228 A | 11/1995 | Franseen et al. | |
| 5,474,444 A * | 12/1995 | Wildman | A61C 7/12 433/18 |
| 5,474,445 A | 12/1995 | Voudouris | |
| 5,505,616 A | 4/1996 | Harwell | |
| 5,522,725 A | 6/1996 | Jordan et al. | |
| 5,545,037 A | 8/1996 | Takeshi | |
| 5,556,277 A | 9/1996 | Yawata et al. | |
| 5,562,445 A | 10/1996 | DeVincenzo et al. | |
| 5,588,833 A | 12/1996 | Risse | |
| 5,595,484 A | 1/1997 | Orikasa et al. | |
| 5,597,302 A | 1/1997 | Pospisil et al. | |
| 5,607,301 A | 3/1997 | Roman | |
| 5,616,026 A | 4/1997 | Cash | |
| 5,618,175 A | 4/1997 | Reher et al. | |
| 5,620,321 A | 4/1997 | Thornburg et al. | |
| 5,622,494 A | 4/1997 | Andreiko et al. | |
| 5,653,588 A | 8/1997 | Moschik | |
| 5,685,711 A | 11/1997 | Hanson | |
| 5,692,898 A | 12/1997 | Orikasa et al. | |
| 5,707,231 A | 1/1998 | Watt et al. | |
| 5,720,611 A | 2/1998 | Teng | |
| 5,727,941 A | 3/1998 | Kesling | |
| 5,729,768 A | 3/1998 | Fields et al. | |
| 5,738,514 A | 4/1998 | DeVincenzo et al. | |
| 5,746,592 A | 5/1998 | Nezu et al. | |
| 5,746,594 A | 5/1998 | Jordan et al. | |
| RE35,863 E | 7/1998 | Sachdeva et al. | |
| 5,779,470 A | 7/1998 | Kussick | |
| 5,791,897 A | 8/1998 | Wildman | |
| 5,810,583 A | 9/1998 | Doyle | |
| 5,820,371 A | 10/1998 | Forster | |
| 5,829,972 A | 11/1998 | Farzin-Nia | |
| 5,829,975 A | 11/1998 | Gold | |
| 5,857,849 A | 1/1999 | Kurz | |
| 5,871,350 A | 2/1999 | Clark et al. | |
| 5,879,157 A | 3/1999 | Schue | |
| 5,885,073 A | 3/1999 | Kussick | |
| 5,885,074 A | 3/1999 | Hanson | |
| 5,890,891 A | 4/1999 | Doyle | |
| 5,908,293 A | 6/1999 | Voudouris | |
| 5,915,550 A | 6/1999 | Gartz | |
| 6,036,489 A | 3/2000 | Brosius | |
| 6,053,458 A | 4/2000 | Meyer | |
| 6,053,729 A | 4/2000 | Brehm et al. | |
| 6,053,759 A | 4/2000 | Kunert et al. | |
| 6,071,119 A | 6/2000 | Christoff et al. | |
| 6,086,364 A | 7/2000 | Brunson | |
| 6,109,916 A | 8/2000 | Wilcko et al. | |
| 6,123,544 A | 9/2000 | Cleary | |
| 6,126,441 A | 10/2000 | Tenti | |
| 6,142,775 A | 11/2000 | Hansen et al. | |
| 6,162,051 A | 12/2000 | Brehm et al. | |
| 6,190,165 B1 | 2/2001 | Andreiko et al. | |
| 6,193,508 B1 | 2/2001 | Georgakis | |
| 6,206,690 B1 | 3/2001 | Vargas | |
| 6,217,322 B1 | 4/2001 | Kesling | |
| 6,220,857 B1 | 4/2001 | Abels | |
| 6,227,849 B1 | 5/2001 | Brehm et al. | |
| 6,234,792 B1 | 5/2001 | DeVincenzo | |
| 6,264,469 B1 | 7/2001 | Moschik | |
| 6,276,930 B1 | 8/2001 | Pozzi | |
| 6,280,185 B1 | 8/2001 | Palmer et al. | |
| 6,302,688 B1 | 10/2001 | Jordan et al. | |
| 6,347,939 B2 | 2/2002 | Abels | |
| 6,354,834 B2 | 3/2002 | Kanomi | |
| 6,358,043 B1 | 3/2002 | Mottate et al. | |
| 6,358,046 B1 | 3/2002 | Brehm et al. | |
| 6,361,314 B1 | 3/2002 | Garton, Jr. | |
| 6,361,317 B1 | 3/2002 | Rahman | |
| 6,368,105 B1 | 4/2002 | Voudouris et al. | |
| 6,371,760 B1 * | 4/2002 | Zavilenski | A61C 7/16 433/8 |
| 6,394,798 B1 | 5/2002 | Huff et al. | |
| 6,428,314 B1 | 8/2002 | Jones, Jr. et al. | |
| 6,461,157 B1 | 10/2002 | Kussick | |
| 6,478,579 B1 | 11/2002 | Brusse | |
| 6,491,519 B1 | 12/2002 | Clark et al. | |
| 6,506,049 B2 | 1/2003 | Hanson | |
| 6,582,226 B2 | 6/2003 | Jordan et al. | |
| 6,592,366 B2 | 7/2003 | Triaca et al. | |
| 6,607,383 B2 | 8/2003 | Abels et al. | |
| 6,616,445 B2 | 9/2003 | Abels et al. | |
| 6,655,957 B2 | 12/2003 | Abels et al. | |
| 6,655,958 B2 | 12/2003 | Abels et al. | |
| 6,656,767 B1 | 12/2003 | King et al. | |
| 6,659,766 B2 | 12/2003 | Abels et al. | |
| 6,659,767 B2 | 12/2003 | Abels et al. | |
| 6,663,385 B2 | 12/2003 | Tepper | |
| 6,668,834 B1 | 12/2003 | Zikria | |
| 6,695,612 B2 | 2/2004 | Abels et al. | |
| 6,705,862 B2 | 3/2004 | Schultz | |
| 6,709,268 B2 | 3/2004 | Pospisil et al. | |
| 6,733,286 B2 | 5/2004 | Abels et al. | |
| 6,769,910 B1 | 8/2004 | Pantino | |
| 6,776,613 B2 | 8/2004 | Orikasa | |
| 6,776,614 B2 | 8/2004 | Wiechmann et al. | |
| 6,846,178 B2 | 1/2005 | Freeman, Jr. et al. | |
| 6,863,528 B2 | 3/2005 | Lin | |
| 6,877,982 B2 | 4/2005 | Williams | |
| 6,893,257 B2 | 5/2005 | Kelly | |
| 6,903,262 B2 | 6/2005 | Blersch | |
| 6,910,884 B2 | 6/2005 | Kelly et al. | |
| 6,913,459 B2 | 7/2005 | Fukutomi | |
| 7,001,179 B2 | 2/2006 | Devincenzo | |
| 7,025,591 B1 | 4/2006 | Kesling | |
| 7,033,170 B2 | 4/2006 | Cordato | |
| 7,033,171 B2 | 4/2006 | Wilkerson | |
| 7,055,908 B1 | 6/2006 | Williams | |
| 7,074,037 B2 * | 7/2006 | Macchi | A61C 7/14 433/10 |
| 7,094,052 B2 | 8/2006 | Abels et al. | |
| 7,140,875 B2 | 11/2006 | Lai et al. | |
| 7,151,541 B2 | 12/2006 | Seder | |
| 7,153,130 B2 | 12/2006 | Christoff | |
| 7,210,927 B2 | 5/2007 | Abels et al. | |
| 7,234,935 B2 | 6/2007 | Abels et al. | |
| 7,247,018 B2 | 7/2007 | Freeman et al. | |
| 7,258,545 B2 | 8/2007 | Hotta | |
| 7,267,545 B2 | 9/2007 | Oda | |
| 7,306,458 B1 | 12/2007 | Lu | |
| 7,416,408 B2 | 8/2008 | Farzin-Nia et al. | |
| 7,442,039 B2 | 10/2008 | Opin et al. | |
| 7,621,743 B2 | 11/2009 | Bathen et al. | |
| 7,695,277 B1 | 4/2010 | Stevens | |
| 7,704,072 B2 | 4/2010 | Damon | |
| 7,780,443 B2 | 8/2010 | Hagelganz | |
| 7,811,087 B2 | 10/2010 | Wiechmann et al. | |
| 7,850,451 B2 | 12/2010 | Wiechmann et al. | |
| 7,909,603 B2 | 3/2011 | Oda | |
| 7,959,437 B2 | 6/2011 | Zakhem | |
| 7,963,768 B2 | 6/2011 | Hilliard | |
| 8,251,697 B2 | 8/2012 | Smith et al. | |
| 8,376,739 B2 | 2/2013 | Dupray et al. | |
| 8,485,816 B2 * | 7/2013 | Macchi | A61C 7/14 433/10 |

(56) References Cited

U.S. PATENT DOCUMENTS

| | | | |
|---|---|---|---|
| 8,573,971 | B2 | 11/2013 | Stevens |
| 8,585,399 | B2 | 11/2013 | Smith et al. |
| 8,678,818 | B2 | 3/2014 | Dupray et al. |
| 8,807,997 | B2 | 8/2014 | Smith et al. |
| 8,961,172 | B2 | 2/2015 | Dupray et al. |
| 8,979,528 | B2 | 3/2015 | Macchi et al. |
| 9,144,473 | B2 * | 9/2015 | Aldo .................. A61C 7/14 |
| RE45,904 | E | 3/2016 | Rudman |
| 9,345,553 | B2 | 5/2016 | Andreiko et al. |
| 9,554,875 | B2 | 1/2017 | Gualano |
| 9,561,089 | B2 | 2/2017 | Smith et al. |
| 9,597,166 | B2 | 3/2017 | Upchurch, Jr. et al. |
| 2001/0036615 | A1 | 11/2001 | Binder |
| 2002/0025502 | A1 | 2/2002 | Williams |
| 2002/0110778 | A1 | 8/2002 | Abels et al. |
| 2002/0187452 | A1 | 12/2002 | Abels et al. |
| 2003/0049582 | A1 | 3/2003 | Abels et al. |
| 2003/0064344 | A1 | 4/2003 | Vazquez |
| 2003/0088261 | A1 | 5/2003 | Schraga |
| 2003/0096209 | A1 | 5/2003 | Sugiyama et al. |
| 2003/0143509 | A1 | 7/2003 | Kopelman et al. |
| 2003/0180678 | A1 * | 9/2003 | Kesling .................. A61C 7/143 433/8 |
| 2004/0244149 | A1 | 12/2004 | Anscher |
| 2004/0259048 | A1 * | 12/2004 | Balabanovsky ......... A61C 7/14 433/10 |
| 2005/0069833 | A1 | 3/2005 | Chikami |
| 2005/0244777 | A1 | 11/2005 | Schultz |
| 2006/0014116 | A1 * | 1/2006 | Maijer .................. A61C 7/12 433/11 |
| 2006/0019212 | A1 * | 1/2006 | Macchi .................. A61C 7/14 433/14 |
| 2006/0046224 | A1 | 3/2006 | Sondhi et al. |
| 2006/0063123 | A1 | 3/2006 | Cleary et al. |
| 2006/0099544 | A1 | 5/2006 | Lai et al. |
| 2006/0099545 | A1 | 5/2006 | Lai et al. |
| 2006/0166158 | A1 | 7/2006 | Abels et al. |
| 2006/0172251 | A1 | 8/2006 | Voudouris |
| 2006/0199137 | A1 | 9/2006 | Abels et al. |
| 2006/0228662 | A1 | 10/2006 | Lokar et al. |
| 2006/0228664 | A1 | 10/2006 | Castner et al. |
| 2006/0234180 | A1 | 10/2006 | Huge et al. |
| 2006/0246392 | A1 | 11/2006 | Vigolo |
| 2006/0252002 | A1 | 11/2006 | Hanson |
| 2006/0257810 | A1 | 11/2006 | Maijer et al. |
| 2006/0263737 | A1 | 11/2006 | Oda |
| 2006/0269889 | A1 | 11/2006 | Voudouris |
| 2007/0009849 | A1 | 1/2007 | Wool |
| 2007/0054231 | A1 | 3/2007 | Manemann et al. |
| 2007/0092849 | A1 | 4/2007 | Cosse |
| 2007/0166658 | A1 | 7/2007 | Voudouris |
| 2007/0172112 | A1 | 7/2007 | Paley et al. |
| 2007/0207436 | A1 | 9/2007 | Tan et al. |
| 2007/0224569 | A1 | 9/2007 | Oda |
| 2007/0243497 | A1 | 10/2007 | Voudouris |
| 2007/0248926 | A1 | 10/2007 | Lai et al. |
| 2007/0256694 | A1 | 11/2007 | Kussick |
| 2007/0259301 | A1 | 11/2007 | Hagelganz et al. |
| 2007/0264606 | A1 | 11/2007 | Muha |
| 2007/0281269 | A1 | 12/2007 | Forster |
| 2008/0014544 | A1 | 1/2008 | Nucera |
| 2008/0128297 | A1 | 6/2008 | Rose |
| 2008/0131831 | A1 | 6/2008 | Abels et al. |
| 2008/0138759 | A1 | 6/2008 | Kravitz et al. |
| 2008/0160474 | A1 | 7/2008 | Wolf et al. |
| 2008/0182219 | A1 | 7/2008 | Spalty |
| 2008/0223377 | A1 | 9/2008 | Kussick |
| 2008/0227047 | A1 | 9/2008 | Lowe et al. |
| 2008/0268398 | A1 | 10/2008 | Cantarella |
| 2009/0004617 | A1 | 1/2009 | Oda et al. |
| 2009/0004618 | A1 | 1/2009 | Oda et al. |
| 2009/0004619 | A1 | 1/2009 | Oda et al. |
| 2009/0042160 | A1 | 2/2009 | Ofir |
| 2009/0162807 | A1 | 6/2009 | Hagelganz et al. |
| 2009/0220907 | A1 | 9/2009 | Suyama |
| 2009/0291404 | A1 | 11/2009 | Oda |
| 2009/0325118 | A1 | 12/2009 | Lewis et al. |
| 2010/0003632 | A1 | 1/2010 | Ruiz Diaz et al. |
| 2010/0062387 | A1 | 3/2010 | Hilliard |
| 2010/0129765 | A1 | 5/2010 | Mohr et al. |
| 2010/0159411 | A1 | 6/2010 | Oda |
| 2010/0178629 | A1 | 7/2010 | Oda et al. |
| 2010/0196840 | A1 | 8/2010 | Lai et al. |
| 2010/0203463 | A1 | 8/2010 | Huff |
| 2010/0261131 | A1 | 10/2010 | Ruiz-Vela et al. |
| 2010/0279247 | A1 | 11/2010 | Kesling |
| 2010/0285420 | A1 | 11/2010 | Oda |
| 2010/0285421 | A1 | 11/2010 | Heiser |
| 2010/0304321 | A1 | 12/2010 | Patel |
| 2011/0014583 | A1 | 1/2011 | Romano et al. |
| 2011/0020762 | A1 | 1/2011 | Kanomi et al. |
| 2011/0039224 | A1 | 2/2011 | Cosse |
| 2011/0076633 | A1 | 3/2011 | Bryant |
| 2011/0081622 | A1 | 4/2011 | Mashouf |
| 2011/0086322 | A1 | 4/2011 | Baron et al. |
| 2011/0123942 | A1 | 5/2011 | Rudman et al. |
| 2011/0165532 | A1 | 7/2011 | Benvegnu' et al. |
| 2011/0287378 | A1 | 11/2011 | Dupray et al. |
| 2012/0070797 | A1 | 3/2012 | Edgren |
| 2013/0280670 | A1 | 10/2013 | Edgren |
| 2013/0309624 | A1 | 11/2013 | Smith et al. |
| 2014/0067335 | A1 | 3/2014 | Andreiko |
| 2014/0370454 | A1 | 12/2014 | Rudman |
| 2015/0173858 | A1 | 6/2015 | Dupray et al. |
| 2015/0182304 | A1 | 7/2015 | Gualano |
| 2016/0008099 | A1 | 1/2016 | Macchi |
| 2016/0175072 | A1 | 6/2016 | Andreiko et al. |
| 2016/0256238 | A1 | 9/2016 | Andreiko et al. |
| 2017/0000588 | A1 | 1/2017 | Alauddin et al. |
| 2017/0112597 | A1 | 4/2017 | Smith et al. |
| 2017/0128160 | A1 | 5/2017 | Gualano |

FOREIGN PATENT DOCUMENTS

| | | |
|---|---|---|
| EP | 0317098 | 5/1989 |
| EP | 0379668 | 8/1990 |
| EP | 0389223 | 9/1990 |
| EP | 0397533 | 11/1990 |
| EP | 0588961 | 3/1994 |
| EP | 0624354 | 11/1994 |
| EP | 0875211 | 11/1998 |
| EP | 1332727 | 8/2003 |
| EP | 1359859 | 11/2003 |
| ES | 2130174 | 7/1999 |
| FR | 2497657 | 7/1982 |
| FR | 2887135 | 12/2006 |
| JP | S60-113016 | 7/1985 |
| JP | S64-25847 | 1/1989 |
| JP | H01-20658 | 6/1989 |
| JP | H02-147112 | 12/1990 |
| JP | H03-21236 | 1/1991 |
| JP | H06-507803 | 9/1994 |
| JP | 2579431 | 2/1997 |
| JP | 11-276504 | 10/1999 |
| JP | 2003-102749 | 4/2003 |
| JP | 2009-535160 | 10/2009 |
| JP | U3155836 | 11/2009 |
| WO | WO 91/07925 | 6/1991 |
| WO | WO 92/00041 | 1/1992 |
| WO | WO 92/20296 | 11/1992 |
| WO | WO 04/039276 | 5/2004 |

OTHER PUBLICATIONS

U.S. Appl. No. 11/123,470, filed May 5, 2005, Wilson.
U.S. Appl. No. 13/199,828, filed Sep. 9, 2011, Rudman et al.
U.S. Appl. No. 13/506,513, filed Apr. 23, 2012, Rudman et al.
U.S. Appl. No. 15/048,519, filed Feb. 19, 2016, Rudman.
U.S. Appl. No. 15/380,814, filed Dec. 15, 2016, Edgren.
U.S. Appl. No. 15/453,465, filed Mar. 8, 2017, Upchurch et al.
3M Unitek Corporation Catalog, 1990, pp. 1-1, 1-3, 3-7, Figs. A, B.
"Buccal Tube," Sankin, printed Apr. 1, 2004, 7 pages.

(56) References Cited

OTHER PUBLICATIONS

"Direct Bond Tubes," American Orthodontics, New Products Catalog, 2005, p. 76.
"Focus on Brackets," Orthodontic Products, Mar. 2005. pp. 1-2.
Ortho Organizers, Inc, Advertisement, "Journal of Clinical Orthodontics," Sep. 1989; 3 pages.
Victory Series Appliance System, Mastering the Art of Orthodontic Application, 3M Unitek Dental Products Division, 1998, 4 pages.
Epstein, "Bi-Dimensional Orthos Treatment: Benefits and Rationale of Differential Bracket-Slot Sizes," Clinical Impressions, 1998, vol. 7(3), 6 pages.
Ricketts, "Provocations and Perceptions in Cranio-Facial Orthopedics," RMO, Inc., Denver, CO, USA, 1989, cover and pp. 982-1021.
U.S. Appl. No. 10/284,016 filed Oct. 29, 2002, now U.S. Pat. No. 6,846,178.
U.S. Appl. No. 10/848,929 filed May 18, 2004 now U.S. Pat. No. 7,247,018.
U.S. Appl. No. 11/782,569 filed Jul. 24, 2007 now U.S. Pat. No. 7,959,437.
U.S. Appl. No. 13/117,070 filed May 26, 2011.
U.S. Appl. No. 13/654,021 filed Oct. 17, 2012 no U.S. Pat. No. 6,597,166.
U.S. Appl. No. 15/453,465 filed Mar. 8, 2017.
U.S. Appl. No. 11/260,923 filed Oct. 27, 2005 now U.S. Pat. No. 7,695,277.
U.S. Appl. No. 12/758,090 filed Apr. 12, 2010 now U.S. Pat. No. 8,573,971.
U.S. Appl. No. 11/852,057 filed Sep. 7, 2007 now U.S. Pat. No. 8,251,697.
U.S. Appl. No. 13/595,548 filed Aug. 27, 2012 now U.S. Pat. No. 8,585,399.
U.S. Appl. No. 14/049,730 filed Oct. 9, 2013 now U.S. Pat. No. 8,807,997.
U.S. Appl. No. 14/459,750 filed Aug. 14, 2014 now U.S. Pat. No. 9,561,089.
U.S. Appl. No. 15/401,718 filed Jan. 9, 2017.
U.S. Appl. No. 12/724,159 filed Mar. 15, 2010 now U.S. Pat. No. 8,485,816.
U.S. Appl. No. 13/762,994 filed Feb. 8, 2013 now U.S. Pat. No. 8,979,528.
U.S. Appl. No. 13/939,937 filed Jul. 11, 2013 now U.S. Pat. No. 9,144,473.
U.S. Appl. No. 14/658,781 filed Mar. 16, 2015.
U.S. Appl. No. 13/240,850 filed Sep. 22, 2011.
U.S. Appl. No. 13/919,545 filed Jun. 17, 2013.
U.S. Appl. No. 15/380,814 filed Dec. 15, 2016.
U.S. Appl. No. 13/117,085 filed May 26, 2011 now U.S. Pat. No. 8,376,739.
U.S. Appl. No. 13/776,997 filed Feb. 14, 2013 now U.S. Pat. No. 8,678,818.
U.S. Appl. No. 14/223,194 filed Mar. 24, 2014 now U.S. Pat. No. 8,961,172.
U.S. Appl. No. 14/627,137 filed Feb. 20, 2015.
U.S. Appl. No. 13/199,828 filed Sep. 9, 2011.
U.S. Appl. No. 13/506,513 filed Apr. 23, 2012.
U.S. Appl. No. 13/762,455 filed Feb. 8, 2013.
U.S. Appl. No. 14/743,142 filed Jun. 18, 2015.
U.S. Appl. No. 15/410,250 filed Jan. 19, 2017.

* cited by examiner

ORTHODONTIC BRACKET HAVING AN ARCHWIRE CHANNEL AND ARCHWIRE RETAINING MECHANISM

CROSS REFERENCE TO RELATED APPLICATIONS

This application is a continuation of U.S. patent application Ser. No. 13/939,937, filed on Jul. 11, 2013 (now U.S. Pat. No. 9,144,473, issued Sep. 29, 2015), which is a continuation of U.S. patent application Ser. No. 12/724,159, filed Mar. 15, 2010 (now U.S. Pat. No. 8,485,816, issued Jul. 16, 2013), and claims the benefit of U.S. Provisional Patent Application Ser. No. 61/160,653, filed Mar. 16, 2009. The entire disclosure of the prior application hereinabove is incorporated herein fully by reference.

RELATED FIELD OF THE INVENTION

The present invention is related to orthodontic brackets, and in particular, to such brackets wherein one or more archwires can be secured in laterally entered archwire retaining channels.

SUMMARY OF THE INVENTION

An orthodontic bracket is disclosed herein for retaining one or more archwires in position. The bracket includes a base having a tooth affixing side and an opposing side, and there is one or more archwire retention channels extending in the mesial-distal directions. Each of the archwire retention channels includes a pair of inverted archwire retaining regions on one side of the channel, wherein each of the retaining regions, in turn, includes a recess that opens generally towards an opposing side of the channel, the opposing side being, in one embodiment, part of the bracket base. Each such recess is for grasping or holding an archwire within the channel having the recess. A first of the archwire retention channels includes a first pair of gingivally located inverted archwire retaining regions whose recesses hold a common archwire. In an embodiment of the bracket having more than one archwire retention channel, a second of the archwire retention channels includes a second pair of occlusally located inverted archwire retaining regions whose recesses hold another archwire. Moreover, for each of the archwire retention channel(s), there is a corresponding archwire retaining ridge extending gingivally-occlusally along the opposing side bracket base between the two archwire retaining regions of the channel, wherein this retaining ridge contacts a portion of an archwire that faces away from the archwire portion being held in the recesses of the inverted archwire retaining regions for the channel. Accordingly, for each pair of archwire retaining regions and an archwire held by the pair, the corresponding archwire retaining ridge exerts a force on the archwire directed toward the interiors of the recesses of the inverted retaining regions of the pair. In particular, this force assists in seating the archwire in the retaining regions of the pair.

Figure 2A:
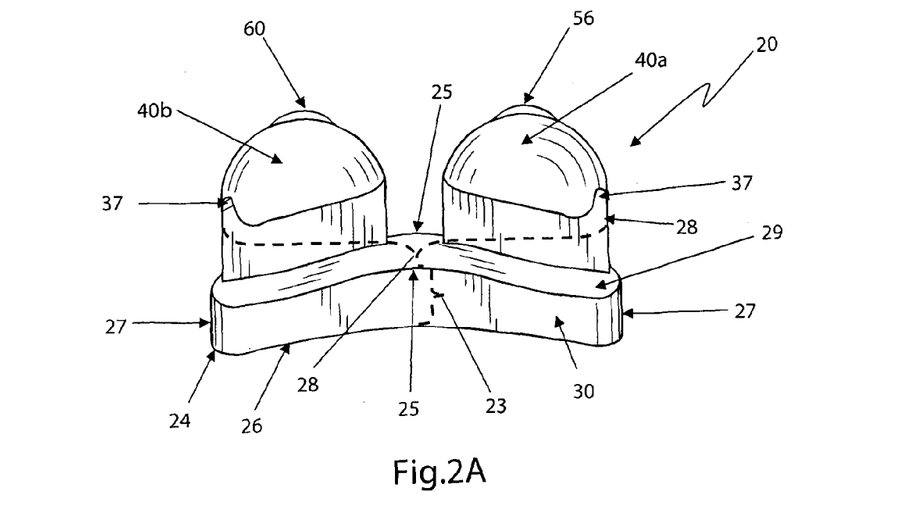
FIG. 2A is a gingival view of the bracket 20 of FIG. 1, wherein the retaining ridge 25 and the archwire retention channel 28 are shown.
Figure 2B:
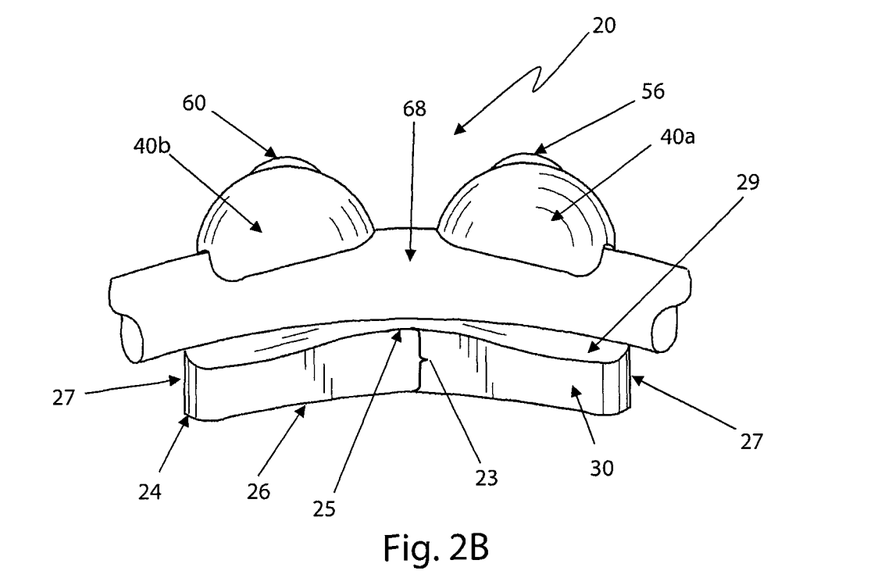
FIG. 2B is a gingival view of the bracket of FIG. 1 with an archwire 68 passing through archwire retention channel 28 (as shown in FIG. 2A), wherein the archwire is held in place in the retaining regions 40a,b by, e.g., the retaining ridge 25.

In particular for the at least one of the archwire retention channel included in the bracket and an archwire provided therein, the elasticity of the archwire to retain an initial non-curved shape causes the archwire to resist a channel induced bow in the archwire (such bowing or curving shown in FIG. 2B). Thus, as an orthodontist positions the archwire in the at least one channel of the bracket, the corresponding retaining regions for the channel together with the corresponding retaining ridge, bind or wedge the archwire within the channel. Accordingly, the opposing forces between the channel and archwire secure the archwire within the channel. Thus, it is a feature of the bracket 20 that for each such archwire channel, there are channel archwire bowing portions that retain the archwire within the channel, wherein a spaced apart plurality of these bowing portions (e.g., 40a and 40b for channel 28) contact the archwire at spaced apart locations on one side of the archwire's length, and wherein between such locations, there is at least one additional channel archwire bowing portion on an opposite side of archwire for inducing the archwire to press against the spaced apart plurality of contacting portions. Thus, the spaced apart plurality of bowing portions, and the at least one additional bowing portion induce oppositely directed forces on the archwire (such forces being traverse to the length of the archwire), and causing the archwire to bow or bend somewhat and to press against these bowing portions for holding the archwire within the channel. Said differently, the channel effectively is effectively bowed along its length.

In some embodiments, one archwire retention channel may be configured to provide more than a single bow or bind of the archwire within the channel. In particular, such a channel may be configured so that an archwire contained therein must form at least one "S" shape with the channel.

The novel bracket preferably has a generally square bracket base with opposing mesial-distal sidewalls, and opposing gingival-occlusal sidewalls that extend between the tooth affixing side and the opposing side (also referred to as an "upper side" herein). Each of the above described retaining ridges is provided by a corresponding thickened portion of the bracket base that extends in the gingival-occlusal direction of the bracket approximately along a gingival-occlusal center line of the bracket base. The thickened portion gradually thins in the mesial-distal direction of the bracket, ending with the same thickness as the gingival-occlusal sidewalls.

Two archwire retention bridges are also included on the novel bracket, wherein each end of each bridge includes one of the inverted archwire retaining regions from a different one of the first and second pairs identified above. A central archwire retention channel (positioned between the two archwire retention channels described above) extends in the mesial and distal direction along a central portion of the bracket. This channel is formed by the two archwire retention bridges which enclose spaced apart portions of the archwire retention channel for securing an archwire therein.

Embodiments of the bracket may be made of stainless steel for strength or other materials, including ceramics, plastics, polycrystalline alumina material, alumina (aluminum oxide), and zirconia. The bracket base design allows for the bracket to be used in both direct and indirect bonding to patients' teeth. Embodiments of the bracket may be formed via an injection molding technique.

Such a universal bracket design may be primarily attached to the lingual side of patients' teeth, but for embodiments of the bracket attached the labial/buccal side of a patients' teeth, the bracket base tooth facing curvature may be specific to particular tooth types.

This Summary section is neither intended nor should be construed as being representative of the full extent and scope of the present invention. Various embodiments of the present disclosure are set forth in the attached figures and in the detailed description hereinbelow and as embodied by the claims. Accordingly, this Summary does not contain all of the aspects and embodiments of the present disclosure, and is not meant to be limiting or restrictive in any manner. Furthermore, the disclosure should be understood by those of ordinary skill in the art to encompass obvious improvements and modifications thereto.

BRIEF DESCRIPTION OF THE DRAWINGS

FIGS. 1-8 illustrate various views and embodiments of novel brackets according to the present disclosure. The drawings are not necessarily drawn to scale.

FIG. 4 is a top view of the bracket 20 of FIG. 1.

DETAILED DESCRIPTION

Figure 1:
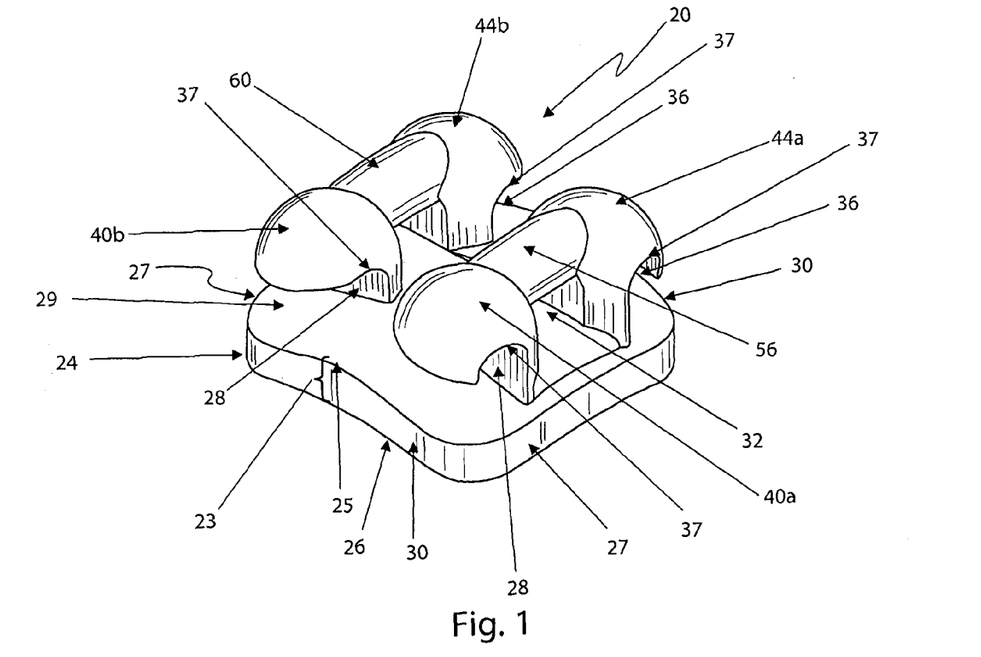
FIG. 1 is a perspective view of a bracket 20 illustrating novel features for an orthodontic bracket.
Figure 3A:
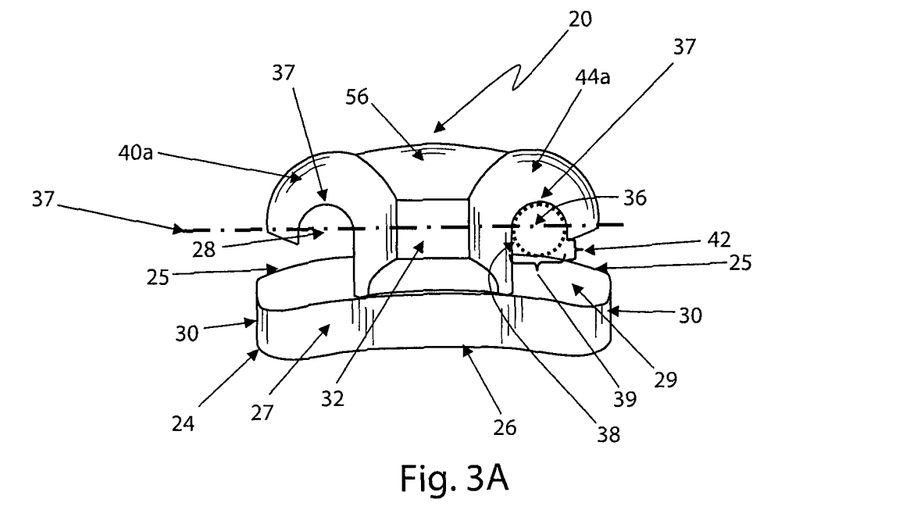
FIGS. 3A and 3B are side views of the bracket 20 of FIG. 1 looking through the archwire retention channels 28, 32 and 36.

Referring to FIGS. 1-8, various embodiments of a bracket 20 are shown, wherein the bracket includes:

(a) A generally square bracket base 24 having an upper side 29, a tooth affixing side 1, opposing mesial-distal sidewalls 27, and opposing gingival-occlusal sidewalls 30 as shown in FIGS. 1, 2A and 2B. Additionally, the bracket base 24 has a pair of retaining ridges 25 extending from each of the opposing gingival-occlusal sidewalls 30 toward the interior of the upper side 29. FIGS. 1 and 2A show one of retaining ridges 25; FIG. 3A shows both retaining ridges. Each of the retaining ridges 25 is provided by a corresponding thickened portion 23 (FIGS. 1, 2A and 2B) of the bracket base 24 that extends in the gingival-occlusal direction of the bracket 20 approximately along a gingival-occlusal center line of the bracket base 24 (e.g., along the line L of FIG. 4). The thickened portion 23 gradually thins in the mesial-distal direction of the bracket 20, ending with the same thickness as the sidewalls 27.

(b) A pair of inverted archwire retaining regions 40a and 40b on the gingival side of the bracket 20 (FIGS. 1 and 2A), and another pair of inverted archwire retaining regions 44a and 44b (FIG. 1) on the occlusal side of the bracket. Each of the pairs (40a,b and 44a,b) is for retaining a respective archwire (e.g., archwire 68, FIG. 2B) therein. In particular, each of the inverted archwire retaining regions 40a and 40b provide a recess 37 (FIGS. 1 and 2A) for grasping or holding an archwire provided therein. Also, each of the inverted archwire retaining regions is attached to (and generally integral with) a corresponding support 39 (FIG. 2A) that connects the retaining region with the bracket base 24. Each support 39 extends outwardly from the upper side 29 by a distance somewhat larger than the cross section of largest archwire to be retained in the recesses 37. Moreover, each of the recesses 37 has an edge 43 (FIGS. 2A,B and 3B) that is spaced apart from the support 39 for the recess, wherein the distance between the edge and the support is also somewhat larger than the cross section of largest archwire to be retained in the recesses 37.

Note that for each of the pairs of the inverted archwire retaining regions 40a,b and 44a,b, a corresponding one of the retaining ridges 25 (FIGS. 1, 2A, 2B and 3A) assists in securing an archwire (e.g., archwire 68) in the two recesses 37 of the pair. Accordingly, for each of the pairs 40a,b and 44a,b, the recesses 37 for the pair operatively cooperate with a corresponding one of the retaining ridges 25 to provide a corresponding archwire retention channel, i.e., for an archwire retention channel 28, the pair 40a,b, defines one side of the channel 28 (i.e., an "outer" side) and the corresponding retaining ridge 25 provides the opposing side of the channel 28 (i.e., an "inner" side), and for an archwire retention channel 36, the pair 44a,b, defines one side of the channel 36 (i.e., an "outer" side) and the corresponding retaining ridge 25 provides the opposing side of the channel 36 (i.e., an "inner" side). Thus, when an archwire is received (and held) in the inverted archwire retaining regions 40a,b or 44a,b (i.e., archwire retention channel 28 or 36), this archwire is operatively coupled together with the bracket attached to a patient's tooth.

(c) Two archwire retention bridges 56 and 60 (FIGS. 1, 2A, 2B, 4, 5A, 6 and 7), wherein each end of each bridge attaches to one of the inverted archwire retaining regions and/or the support 39 therefor. For example, i.e., the ends of the bridge 56 may be attached to the inverted archwire retaining regions 40a and 44a (or attached to the support 39 therefor), and the ends of the bridge 60 may be attached to the inverted archwire retaining regions 40b and 44b (or attached to the support 39 therefor).

(d) An archwire retention channel 32 (FIGS. 1, 3A, and 5A) extending in the mesial and distal direction along a central portion of the bracket 20. The two archwire retention bridges 56 and 60 (together with their corresponding inverted archwire retaining regions) enclose, and substantially define, spaced apart portions of the archwire retention channel 32 for securing an archwire therein (FIG. 8B).

The bracket base 24 may be made of a variety of materials, but in one embodiment may be stainless steel for strength. However, other materials may be used including ceramics and plastics. The remainder of the bracket 20 may be composed of various materials in addition to those recited above (e.g., polycrystalline alumina material, alumina (aluminum oxide), zirconia). In one embodiment, the bracket 20 may be formed via an injection molding technique.

The bracket base 24 may be a universal bracket design in that it can be attached to the surface of various tooth types (e.g., incisor, bicuspid, molar, etc). Moreover, such a universal bracket design does not require bracket identification to aid in identifying placement of the bracket and/or identifying a particular embodiment of the bracket 20. Such a universal bracket design also leads to simplified inventory management since only one embodiment of the bracket 20 may be needed for placement on all teeth types instead of different embodiments of the bracket for different teeth types. However, such universal bracket design may be primarily for the lingual side of patients' teeth. For embodiments of the bracket 20 to be provided on the labial/buccal side of patients' teeth, the curvature of the tooth affixing side 1 may be specific to particular tooth types as one skilled in the art will understand. Accordingly, it is also within the scope of the present disclosure that markings or identifications may be provided on embodiments of the bracket 20 for identifying the bracket (e.g., as a universal bracket, or specific to a particular tooth type(s)), for identifying the manufacturer or distributor of the bracket, and/or for identifying a particular placement or orientation of the bracket on a tooth or tooth type. Note that descriptions of providing such markings and/or identifications are disclosed in U.S. Patent Application Publication 2008/0020338 filed Jul. 24, 2007 and published Jan. 24, 2008, this application being fully incorporated herein by reference.

The bracket base 24 design allows for the bracket 20 to be used in both direct and indirect bonding. Note that the term direct bonding refers to applying adhesive directly to a patient's tooth and subsequently attaching a bracket 20 thereto. Indirect bonding refers to positioning one or more brackets 20 on a dental cast of a patient's teeth. The dental cast, having the brackets 20 attached thereto, is then surrounded with a material, wherein the material, once solidified, secures the brackets therein and can act as a transportation device for the brackets once the dental cast is dissolved away. Adhesive is then applied to the back of each of the brackets 20 prior to placing the transportation device containing the brackets onto the patient's teeth. Accordingly, in the indirect bonding technique, all of the brackets 20 are bonded to the patient's teeth simultaneously. Once the brackets 20 are bonded, the transportation device is removed from the teeth, leaving behind the brackets attached to the teeth.

Regarding the retaining ridges 25 described above, each such ridge corresponds to a maximal offset from the tooth affixing side 1 along a corresponding one of the archwire retention channels 28 and 36. Moreover, in at least some embodiments, such a ridge 25 has its maximal offset centered on line L of FIG. 4. In the embodiment of the bracket 20 shown in FIGS. 2A and 2B, the contour of each of the retaining ridges 25 is a smooth arc without undulations in the mesial-distal direction, and may also be a smooth arc in the gingival-occlusal direction without undulations. However, it is within the scope of the present disclosure that in the gingival-occlusal direction, such a ridge 25 may reach its maximal offset at any point where the ridge transverses its corresponding archwire retention channel (28 or 36) as long as the ridge effectively assists in wedging or holding an archwire in the channel (i.e., the recesses 37 of the channel). Thus, the thickened portion 23 (FIG. 1) for each retaining ridge 25 may induce a force upon an archwire 68 or 64 (e.g., FIG. 5A) to retain it in the archwire retaining regions of the corresponding archwire retention channel 28 or 36. Note that each of the two retaining ridges 25 may have symmetrical profiles (i.e., mirror images of one another about the center line L of FIG. 4, and about mesial-distal center line through the bracket). Moreover, note that the maximal offset for a retaining ridge 25 may occur just outside its corresponding archwire retention channel, e.g., on the mesial-distal perimeter of the channel furthest from the central retention channel 32. Such placements of the maximal offsets may not only provide forces for securing an archwire within the corresponding recesses 37, but also apply a force on the archwire for inhibiting the archwire from moving in a direction generally lateral to the upper side 29.

In another embodiment of the bracket 20, the retaining ridges 25 may have a larger or smaller maximal offset from the tooth affixing side 1 to the upper side 29 of the bracket base 24 when compared to the embodiments of the figures. Moreover, one of the retaining ridges 25 may have a larger maximal offset from the tooth affixing side 1 than the other retaining ridge 25. This variance in the maximal offset of the retaining ridges 25 may allow for and aid in the retention of different diameter archwires in the retaining regions 40a,b and 44a,b.

In another embodiment of the bracket 20, one or more of the retaining ridges 25 may have a corresponding secondary retaining ridge located at the gingival or occlusal edges of the bracket base 24. These secondary retaining ridges may be located on the upper side 29 at the gingival and/or occlusal edges of the bracket base 24. Such secondary retaining ridges may extend in the mesial-distal direction on the upper side 29 of the bracket base 24. The secondary retaining ridges may have varying shapes (e.g., hemispherical or elliptical). Accordingly, the retaining regions 40a,b and 44a,b, in conjunction with the secondary retaining ridges, keep the corresponding archwire secured in one of the corresponding archwire retention channels 28 and 36 (more specifically their recesses 27).

For further description of the archwire retention channels 28, 32 and 36, reference is made to FIG. 3A which provides a lateral (side) view of the bracket 20 along a gingival-occlusal side. The center archwire retention channel 32 of the bracket 20 is enclosed by the two spaced apart portions of the archwire retention bridges 56 and 60 (FIGS. 1, 2A, 2B, 4, 5A, 6 and 7), and the upper side 29 of the bracket base 24. As described above, each of the gingival archwire retention channel 28 and the occlusal archwire retention channel 36 is provided by: (i) partially enclosed spaced apart recesses 27 of a pair of inverted archwire retaining regions, respectively, 40a,b or 44a,b, and (ii) the upper side 29 of the bracket base 24. Both the gingival archwire retention channel 28 and the occlusal archwire retention channel 36 may be mirror images of one another. Each of the inverted archwire retaining regions 40a,b for the gingival archwire retention channel 28, and each of the retaining regions 44a,b for the occlusal archwire retention channel 36 may be generally circular in profile (as shown in, e.g., FIG. 3A). Each such profile may generally match the curvature of, e.g., the cross section of a corresponding archwire to be provided therein. In FIG. 3A, a dashed circular cross section 38 of such an archwire is shown in the archwire retaining regions 44a,b of the occlusal archwire retention channel 36. The diameter 39 of the archwire retention channel 36 may be sufficiently surrounded by the inverted archwire retaining regions 44a,b to grip and retain the archwire therein. In at least one embodiment, the opening 42 for receiving the archwire into the channel 36 is preferably approximately the same size as the diameter of the archwire cross section 38 along the axis 37, e.g., smaller or larger by approximately 0.01 to 0.02 inches. As also illustrated in FIG. 3A, each of the inverted archwire retaining regions 44a,b may surround somewhat more than 180 degrees of the circular cross section of an archwire positioned in the occlusal archwire retention channel 36. Note that a similar description can also be provided for the gingival archwire retention channel 28 in that the channel 28 may be a mirror image of occlusal archwire retention channel 36. However, it is within the scope of the present disclosure that the gingival archwire retention channel 28 may be configured differently from the occlusal archwire retention channel 36, e.g., the gingival archwire retention channel 28 may secure different sizes of archwires therein from the archwires for the occlusal archwire retention channel 36. Also, either or both of the archwire retention channels 28 and 36 may have an elliptical profile or other profile instead of the circular profile shown in FIG. 3A. Further, an embodiment of the bracket 20 may have only one of the archwire retention channels 28 or 36.

Figure 3B:
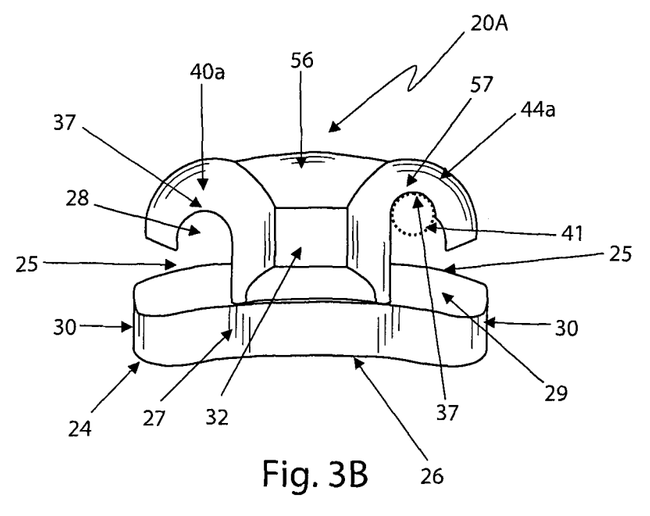

Referring to FIG. 3B, an embodiment of the bracket 20A is shown that includes a retaining region (e.g., 44a) that is shaped or configured to retain archwires having substantially different cross sectional diameters. An archwire having a diameter 39 (FIG. 3A) may be snapped into the retaining region 44a as indicated in FIG. 3A. However, an archwire having a much smaller cross section 41, as shown in FIG. 3B, may also be provided in the channel 36. In particular, the smaller diameter archwire may snap into (or is otherwise retained) in an upper section 57 of the retaining region. Note that in one embodiment, a bead (not shown) may be strung on this smaller diameter archwire such that the bead is positioned between the retaining regions 44a and 44b so that the bead contacts the corresponding retaining ridge 25 for the occlusal archwire retention channel 36 in a manner that assists in locking the archwire into the upper section 57.

Whether the bracket embodiment of FIG. 3A or 3B is provided, multiple sizes of archwires may be utilized in each of the archwire retention channels 28, 32 and 36. The range in the maximal cross sectional extent of the archwires that may be utilized can be from 0.008 inches to 0.024 inches, and such cross sections may be generally circular in cross sectional shape but different cross sectional shapes may be used, e.g., at least rectangular or square cross sectional shapes for the central archwire retention channel 32. The multiple sizes of archwires may provide varying forces and friction levels ranging from an alignment force having a low friction, to a leveling force having a moderate friction, to a finishing force having a maximum friction as one skilled in the art will understand. In particular, the inverted archwire retaining regions 40a,b and 44a,b allow for the archwires 68 or 64 (FIGS. 5A, 6 and 7) to be attached to the bracket 20 without the use of ligatures.

In another embodiment, the archwire retaining regions 40a and 44a (or 40b and 44b) may be joined together, above the upper side 29. Such joining of the retaining regions for one of the archwire retention channels 28 or 1 may form a single integral retaining region, or the joining may be in form of a bridge therebetween similar to the bridges 56 and 60 (except extending in the mesial-distal direction rather than the gingival-occlusal direction). Regardless, there may be a cutout (not shown) over the corresponding retaining ridge 25 so that when the archwire contacts the retaining ridge 25, the archwire is wedged into this cutout. In another embodiment, there may be only one of the outer archwire retention channels 28 and 36 utilized to retain an archwire.

Figure 4:
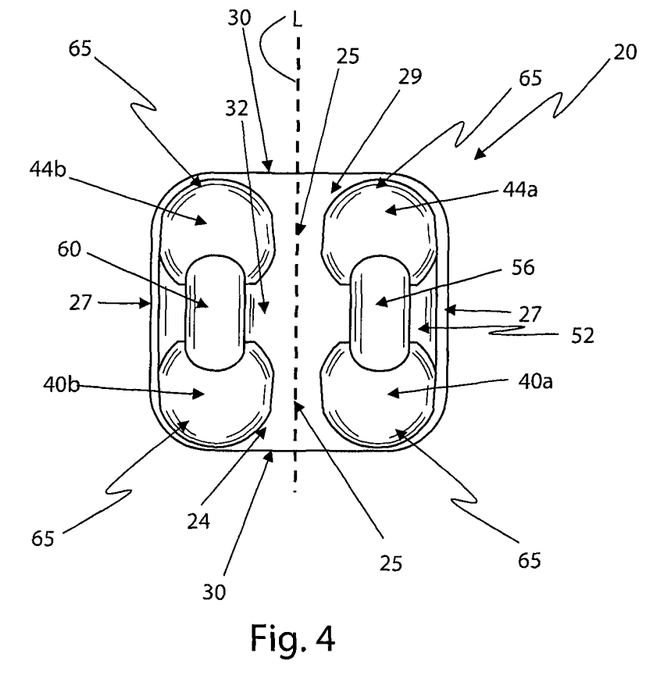

Referring to FIG. 4, a top view of the bracket 20 is shown wherein the center archwire retention channel 32 on the bracket is defined by the spaced apart portions of the archwire retention bridges 56 and 60 and the upper side 29 of the bracket base 24. The archwire retention bridges 56 and 60 connect and reinforce the inverted archwire retaining regions 40a to 44a and 40b to 44b. The smooth rounded contours and edges 65 of the inverted archwire retaining regions 40a,b and 44a,b provide for patient comfort, particularly when such brackets are placed on the lingual side of a patient's teeth. In the center archwire retention channel 32, the archwire is enclosed on all sides (FIGS. 3A and 3B) at two points along the channel, i.e., using the archwire retention bridges 56 and 60 (FIG. 4).

Figure 5:
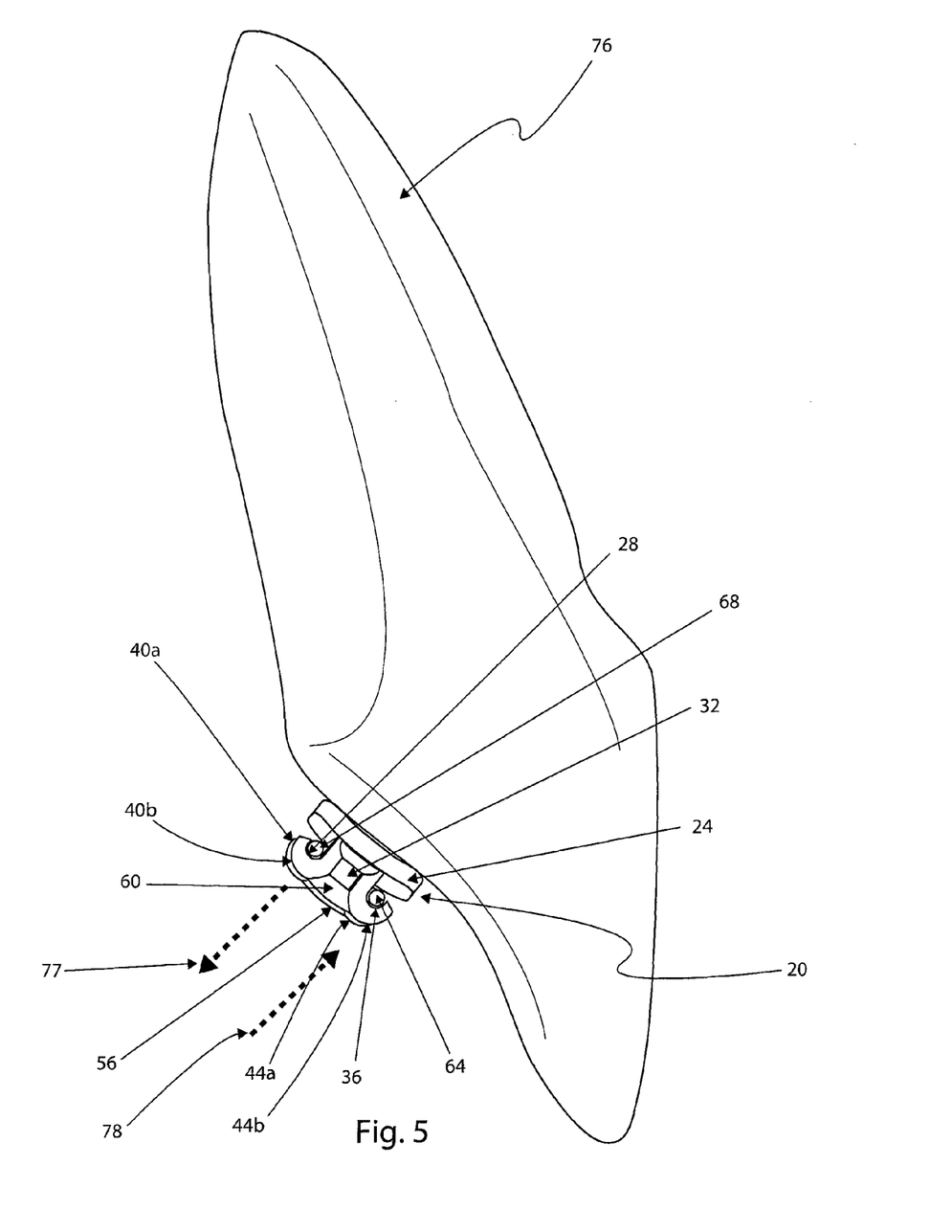
FIG. 5 is lateral perspective view of the bracket 20 of FIG. 1 with archwires 68 and 64 located in the gingival 28 and occlusal 36 archwire retention channels to provide, e.g., torque to a tooth 76 to which the bracket may be attached.

A lateral view of the bracket 20, as shown in FIG. 5, shows an archwire 64 in the occlusal archwire retention channel 36 and an archwire 68 in the gingival archwire retention channel 28. The occlusal 64 and gingival 68 archwires are held place via the friction system created by the inverted archwire retaining regions 40a,b and 44a,b in combination with the ridges 25 (not shown in FIG. 5). FIG. 5 also shows where the bracket 20 may reside on a tooth when it is bonded thereto. The arrows 77 and 78 (FIG. 5) indicate the forces for a torque that the bonded bracket 20 may apply to the tooth.

Figure 6:
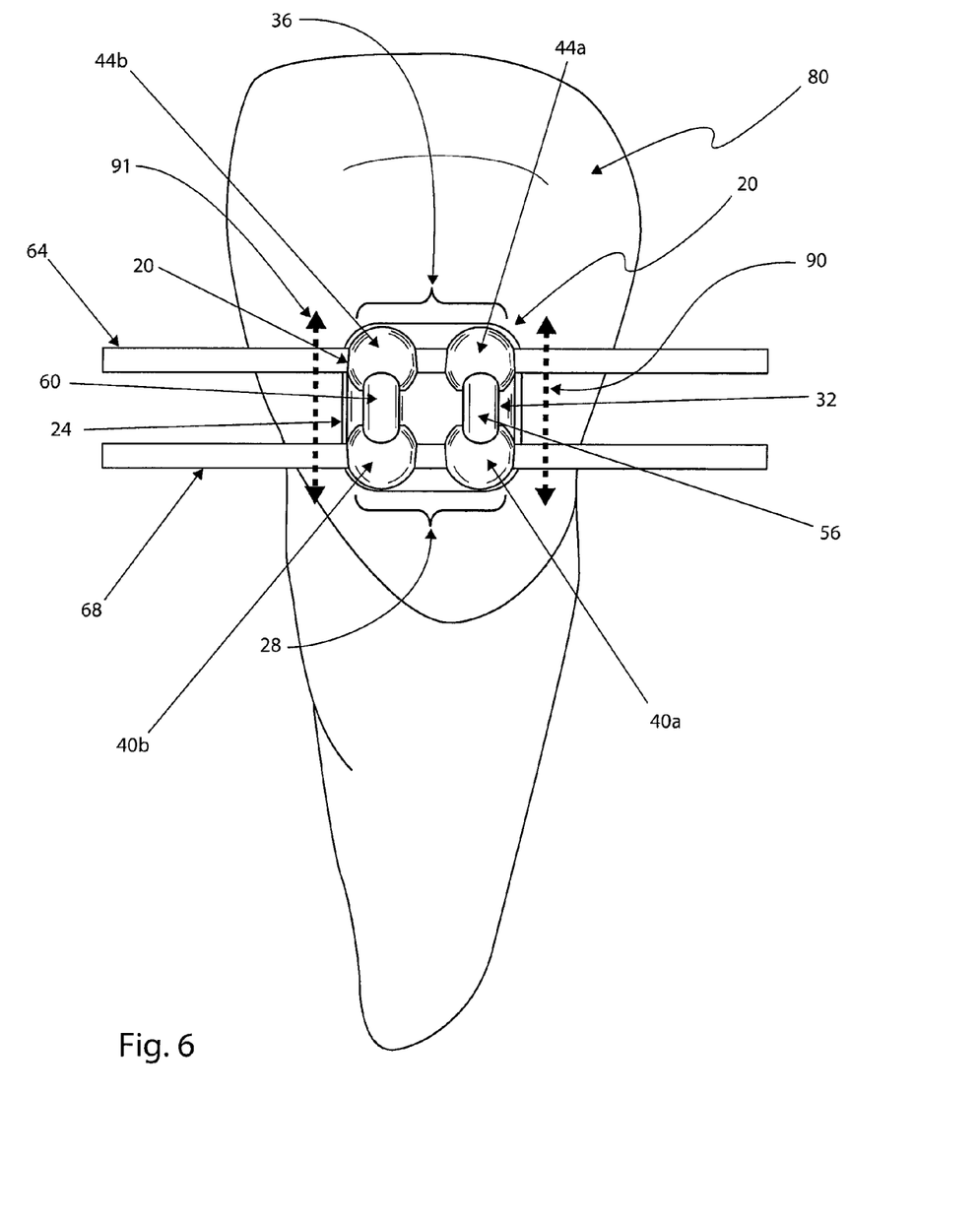
FIG. 6 is a top view of the bracket 20 of FIG. 1 with archwires 68 and 64 located in the gingival 28 and occlusal 36 archwire retention channels to provide tip to the tooth 80 to which the bracket is attached as one skilled in the art will understand.

FIG. 6 provides a top view of the bracket 20 bonded to a tooth 80 wherein there is an archwire 64 in the occlusal archwire retention channel 36, and an archwire 68 in the gingival archwire retention channel 28. The arrows 90 and 91 indicate the motion of tip (angulation) that the bracket 20 may apply to the tooth once it is bonded and the archwires are configured appropriately.

Figure 7:
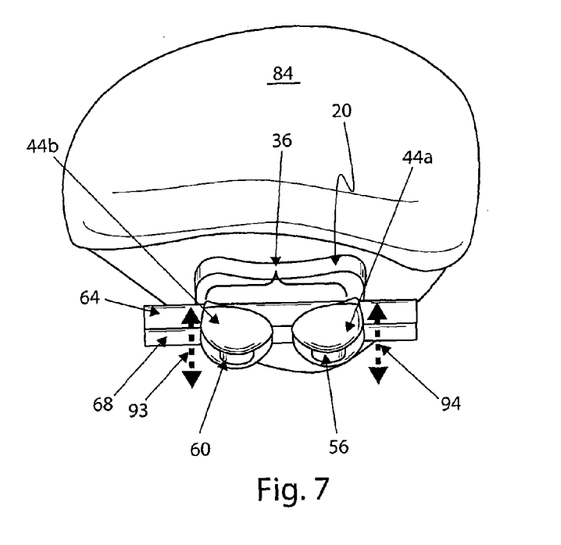
FIG. 7 is an end perspective view of the bracket 20 of FIG. 1 with archwires 68 and 64 located in the gingival 28 (not shown) and occlusal 36 archwire retention channels to provide rotation to the tooth 84 to which the bracket is attached as one skilled in the art will understand.

An end perspective view of the bracket 20 is shown in FIG. 7 with an archwire 64 in the occlusal archwire retention channel 36 and an archwire 68 in the gingival archwire retention channel 28. This figure also shows the bracket bonded to a tooth 84 thereby showing where the bracket 20 may reside on the tooth when it is bonded thereto. The arrows 93 and 94 indicate the motion of rotation that the bracket 20 and the archwires 64 and 68 may apply to the tooth.

Figure 8A:
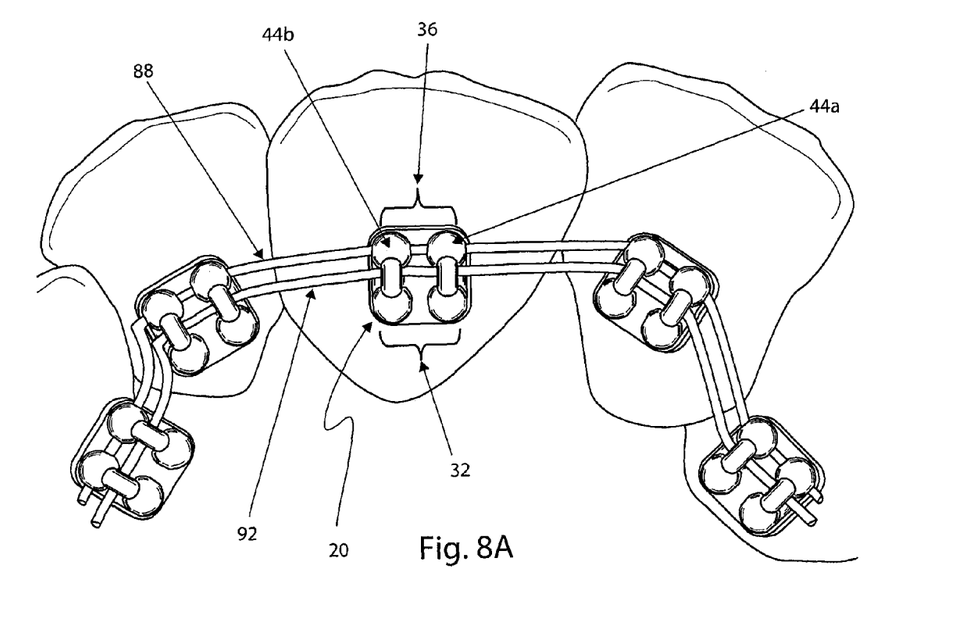
FIGS. 8A and 8B show an embodiment of the novel bracket 20 with different archwire configurations attached thereto.
Figure 8B:
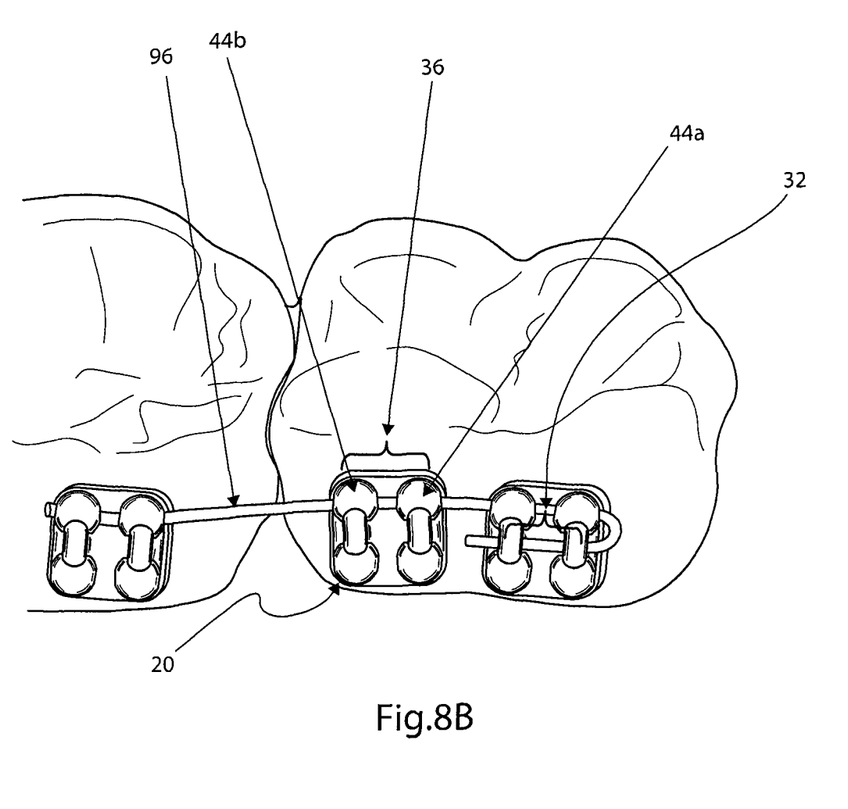

A plurality of the brackets 20 is shown connected together by archwires in FIGS. 8A and 8B. FIG. 8A shows the plurality of brackets 20 connected together by an archwire 88 extending through the corresponding occlusal archwire retention channels 36 of the brackets. FIG. 8A also shows a second archwire 92 secured in the center archwire retention channel 32 of the brackets 20, providing dynamic sectional control in the movement of the teeth, as one skilled in the art will understand. FIG. 8B displays how another configuration, wherein there is an archwire 96 in the occlusal archwire retention channel 36 of the brackets 20. The archwire 96 is also configured so that its end is secured in the center archwire retention channel 32 of the rightmost one of the brackets 20, thereby creating a loop like shape. It is worth noting that due to the diminutive size of the brackets 20 relative to the teeth to which they are attached (as shown in FIGS. 8A and 8B), the size of these brackets 20 may allow for the bonding of two such brackets 20 on a single tooth. For example, FIG. 8B shows two such brackets 20 affixed to a molar.

Alternative embodiments of the bracket 20 include providing the inverted archwire retaining portions so that instead of their recesses 37 opening toward the base 24, such recesses open in another direction (e.g., away from the base, or generally parallel with the upper side 29 of the base). In such embodiments, the retaining ridge 25 is also repositioned to face in the direction toward such recesses for retaining an archwire in the same manner as, e.g., shown in FIG. 2B except that the base 24 in this figure would no longer be the base of the bracket. Instead, the base would attach, e.g., to the top of the retaining portions 40a,b and 44a,b, or alternatively attach the bracket components shown FIG. 2B to a (new) bracket base that is oriented substantially perpendicular to the base shown in FIG. 2B.

In each of the embodiments of the bracket 20 disclosed hereinabove, at least one of the archwire retention channels 28 and 36 is provided, wherein for an archwire provided therein, the elasticity of the archwire to retain an initial non-curved shape causes the archwire to resist the channel induced bow in the archwire (such curving shown in FIG.

2B). Thus, as an orthodontist positions the archwire in the at least one channel of the bracket 20, the corresponding retaining regions (40 and 44) for the channel together with the corresponding retaining ridge 25 bind or wedge the archwire within the at least one channel. Accordingly, the opposing forces between the channel and archwire are believed to secure the archwire within the channel. Thus, it is a feature of the bracket 20 that for each such archwire channel (e.g., 28 and/or 36), there are channel archwire bowing portions that retain the archwire within the channel, wherein a spaced apart plurality of these bowing portions (e.g., 40a and 40b for channel 28) contact the archwire at spaced apart locations on one side of the archwire's length, and wherein between such locations, there is at least one additional channel archwire bowing portion on an opposite side of archwire for inducing the archwire to press against the spaced apart plurality of contacting portions. Thus, the spaced apart plurality of bowing portions, and the at least one additional bowing portion induce oppositely directed forces on the archwire (such forces being traverse to the length of the archwire), and causing the archwire to bow or bend somewhat and to press against these bowing portions for holding the archwire within the channel.

In use, after an orthodontist has secured the bracket 20 to one of a patient's teeth, the orthodontist may exert a force (e.g., substantially parallel to the upper side 29) on a corresponding archwire to force the archwire enter one or both of the archwire retention channels (28 or 36), wherein such force induces the corresponding archwire to bow in the channel. Alternatively, the orthodontist may thread the archwire into such a channel, wherein the orthodontist pushes the archwire into the channel by purposely bowing or binding the archwire to follow the bow of the channel, and then once the archwire is threaded through the channel, the orthodontist can then bend the archwire into the correct orientation to attach the archwire to, e.g., a next orthodontic appliance attached to, e.g., a next tooth. Note, that such subsequent bending of the archwire by the orthodontist is believed to also provide similar forces on the archwire (and traverse to the length thereof) as described above for securing the archwire within the channel.

The disclosure herein describes the best mode known to carry out the invention as claimed in the claims hereinbelow. Moreover, the foregoing disclosure has been provided for purposes of illustration and description. This disclosure is not intended to limit the invention claimed hereinbelow, and various embodiments thereof. Variations, embodiments and modifications will be apparent to those skilled in the art and are intended to be within the scope of the following claims.

What is claimed is:

1. A method for adjustment of a patient's tooth using an orthodontic appliance, wherein the appliance has mesial and distal archwire retaining portions on opposite sides of a bracket with respective retaining ridges, the method comprising: applying a force to an archwire positioned within a patient's mouth for inducing a predetermined bow when the archwire enters an archwire retaining channel, wherein the mesial and distal archwire retaining portions are on a first side of the channel and a retaining ridge is on an opposing side; contacting the archwire at a location between the mesial and distal archwire retaining portions for providing the predetermined bow in the archwire in a direction towards the first side, wherein the archwire has a cross sectional extent from 0.008 inches to 0.024 inches.

2. The method as set forth in claim 1, wherein a shape of the bracket retains the archwire.

3. The method as set forth in claim 1, wherein the archwire retaining portions are configured to grasp the archwire.

4. The method as set forth in claim 1, wherein the archwire retaining portions are configured for mating with more than 180° about the archwire.

5. The method as set forth in claim 1, wherein each of the mesial and distal archwire retaining portions include a configuration for surrounding more than 180° of a cross section of two different archwires, wherein the two different archwires have different cross-sectional extents.

6. The method as set forth in claim 1, wherein the bracket has a base and at least one of the retaining portions has a recess that opens toward the base.

7. The method as set forth in claim 1, wherein the retaining ridge is opposite a gap along the archwire retaining channel.

8. The method as set forth in claim 1, wherein the bracket has a base and at least one of the retaining portions has a recess that opens away from the base.

9. The method as set forth in claim 1, wherein the archwire retaining portions have rounded contours and edges.

10. The method as set forth in claim 1, wherein the archwire retention channel has an elliptical profile.

11. The method of claim 1, wherein the archwire is caused to bow in a fashion that holds the archwire within the archwire retaining channel.

12. The method of claim 1, wherein the archwire retaining portions have smooth contours and edges.

13. The method of claim 1, wherein the archwire is attached to the bracket without the use of ligatures.

14. The method of claim 1, wherein the archwire retaining portions are inverted.

15. A method for adjustment of a patient's tooth using an orthodontic appliance, comprising:
   securing an orthodontic appliance to a patient's tooth, wherein the appliance includes:
   (a) a tooth attachment side for attaching to a tooth, and an outer side for facing away from the tooth;
   (b) mesial and distal archwire retaining portions for retaining an archwire in a first archwire retaining channel, each of the mesial and distal archwire retaining portions having a corresponding recess for receiving the archwire;
   (c) a first retaining ridge for holding the archwire in the corresponding recesses, the first retaining ridge extending away from the tooth attachment side further than distal and mesial ends of the first archwire retaining channel;
   (d) second mesial and distal archwire retaining portions for retaining a second archwire in a second archwire retaining channel, each of the second mesial and distal archwire retaining portions having a corresponding additional recess for receiving the second archwire;
   (e) a first bridge extending between and fixedly connecting the mesial archwire retaining portion and the second mesial archwire retaining portion;
   (f) a second bridge extending between and fixedly connecting the distal archwire retaining portion and the second distal archwire retaining portion; and
   (g) wherein the each of the first and second bridges enclose a part of an archwire retention channel between the first and second archwire retaining channels;
   providing the archwire in an open side along a length of the first archwire retaining channel for receiving the archwire in the first archwire retaining channel;

applying a force to the archwire for inducing a predetermined bow therein when the archwire enters the first archwire retaining channel, wherein the mesial and distal archwire retaining portions are on a first side of the first archwire retaining channel, and the first retaining ridge is on an opposing second side of the first archwire retaining channel, and contacts the archwire at a location between the mesial and distal archwire retaining portions for providing the predetermined bow in the archwire in a direction toward the first side;

providing the second archwire in an open side along a length of the second archwire retaining channel for receiving the archwire in the second archwire retaining channel;

applying a force to the second archwire for inducing a predetermined second bow therein when the second archwire enters the second archwire retaining channel, wherein the second mesial and second distal archwire retaining portions are on a first side of the second archwire retaining channel, and a second retaining ridge is on an opposing second side of the second archwire retaining channel, and contacts the second archwire at a location between the second mesial and second distal archwire retaining portions for providing the predetermined second bow in the second archwire in a direction toward the first side of the second archwire retaining channel;

wherein the archwire retaining portions are configured to grasp the archwire; and wherein the first retaining ridge is opposite a gap along the first archwire retaining channel;

wherein the archwires are generally rectangular or square in cross sectional shape; and wherein the archwire retaining portions are inverted.

16. The method of claim 15, wherein the archwire retaining portions have rounded contours and edges.

17. The method of claim 15, wherein said archwire retaining portions have recess openings directed away from the base.

18. The method of claim 15, wherein the archwire retention channel has an elliptical profile.

19. The method of claim 15, wherein the archwire is attached to the bracket without the use of ligatures.

20. A method for adjustment of a patient's tooth using an orthodontic appliance, wherein the appliance has mesial and distal archwire retaining portions on opposite sides of a bracket with respective retaining ridges, the method comprising applying a force to an archwire positioned within a patient's mouth for inducing a predetermined bow when the archwire enters an archwire retaining channel, wherein the mesial and distal archwire retaining portions are on a first side of the channel and a retaining ridge is on an opposing side contacting the archwire at a location between the mesial and distal archwire retaining portions for providing the predetermined bow in the archwire in a direction towards the first side;

wherein a shape of the bracket retains the archwire;

wherein the archwire retaining portions are configured to grasp the archwire;

wherein said appliance further includes a first bridge extending between and fixedly connected to the distal archwire retaining portions on opposite sides of the bracket;

wherein the archwires have a cross sectional extent from 0.008 inches to 0.024 inches wherein the archwires are generally rectangular or square in cross sectional shape; and wherein the archwire retaining portions are inverted.

* * * * *